United States Patent
Taniguchi et al.

(10) Patent No.: US 9,695,140 B2
(45) Date of Patent: Jul. 4, 2017

(54) GAMMA-BUTYROLACTONE COMPOSITION AND METHOD FOR PRODUCING SAME

(71) Applicant: MITSUBISHI CHEMICAL CORPORATION, Chiyoda-ku (JP)

(72) Inventors: Shohei Taniguchi, Okayama (JP); Yusuke Izawa, Mie (JP); Masaru Utsunomiya, Tokyo (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 15/239,232

(22) Filed: Aug. 17, 2016

(65) Prior Publication Data

US 2016/0355491 A1 Dec. 8, 2016

Related U.S. Application Data

(63) Continuation of application No. PCT/JP2015/054174, filed on Feb. 16, 2015.

(30) Foreign Application Priority Data

Feb. 17, 2014 (JP) ................................. 2014-027766

(51) Int. Cl.
*C07D 307/33* (2006.01)
(52) U.S. Cl.
CPC ................................. *C07D 307/33* (2013.01)
(58) Field of Classification Search
CPC .................................................. C07D 307/33
USPC ........................................................ 549/326
See application file for complete search history.

(56) References Cited

U.S. PATENT DOCUMENTS

| 4,892,955 A | 1/1990 | Wada et al. |
| 5,021,589 A | 6/1991 | Wada et al. |
| 5,401,857 A | 3/1995 | Grey et al. |
| 5,962,700 A | 10/1999 | Heider et al. |
| 2014/0187740 A1 | 7/2014 | Izawa et al. |
| 2016/0264500 A1 | 9/2016 | Izawa et al. |

FOREIGN PATENT DOCUMENTS

| EP | 2 730 555 A1 | 5/2014 |
| JP | 63-277666 | 11/1988 |
| JP | 64-25771 | 1/1989 |
| JP | 7-42279 | 5/1995 |
| JP | 2003-226688 | 8/2003 |
| JP | 2006-143675 | 6/2006 |
| JP | 2013-60428 | 4/2013 |
| WO | WO 2013/008686 A1 | 1/2013 |
| WO | WO 2013/027774 A1 | 2/2013 |

OTHER PUBLICATIONS

Extended European Search Report issued on Oct. 20, 2016 in Patent Application No. 15748955.0.
International Search Report issued May 19, 2015 in PCT/JP2015/054174 filed on Feb. 16, 2015(with English Translation).
Written Opinion Issued May 19, 2015 in PCT/JP2015/054174 filed on Feb. 16, 2015.

*Primary Examiner* — Taofiq A Solola
(74) *Attorney, Agent, or Firm* — Oblon, McClelland, Maier & Neustadt, L.L.P.

(57) ABSTRACT

An object of the present invention is to provide high-purity gamma-butyrolactone (GBL) capable of preventing occurrence of reaction other than the object at the time of use, which reaction is caused due to a high acidity of GBL, and the present invention relates to a gamma-butyrolactone composition containing gamma-butyrolactone and a nitrogen-containing compound, wherein a content of the gamma-butyrolactone is 99.0% by mass or more, and a total content of the nitrogen-containing compound is 0.1 ppm by mass to 1,000 ppm by mass as converted to a nitrogen atom.

9 Claims, 1 Drawing Sheet

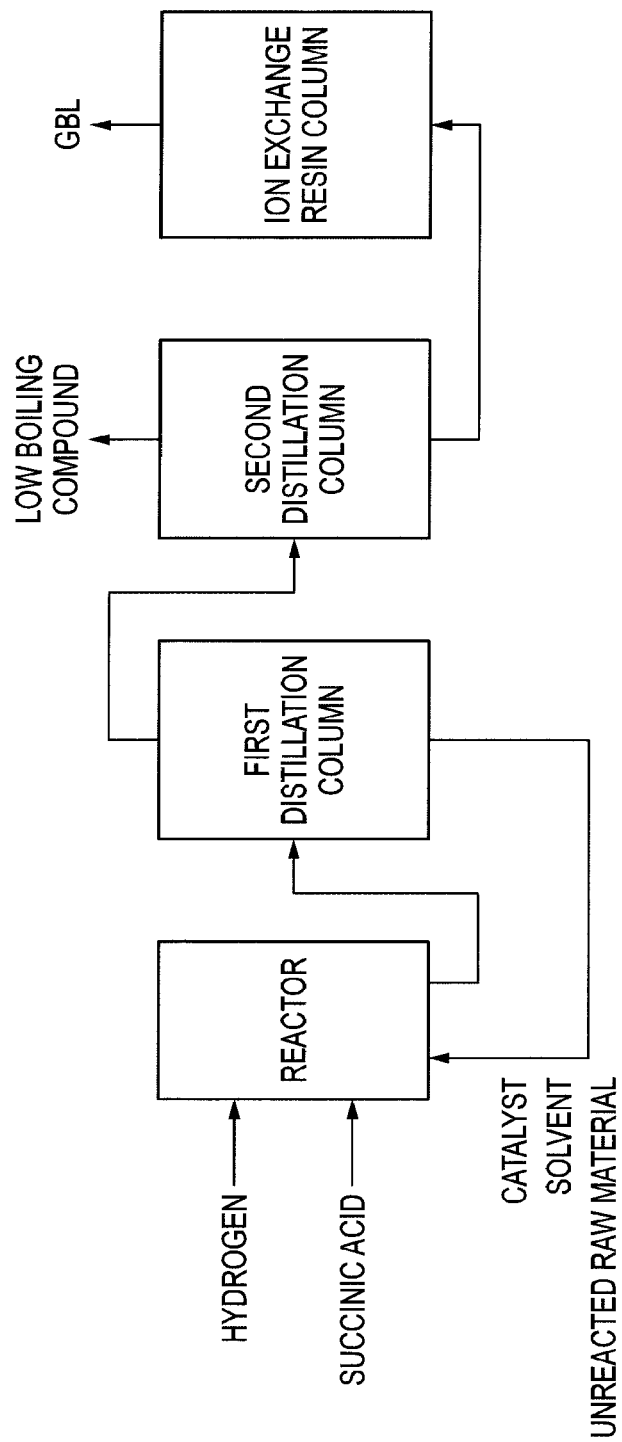

GAMMA-BUTYROLACTONE COMPOSITION AND METHOD FOR PRODUCING SAME

TECHNICAL FIELD

The present invention relates to a gamma-butyrolactone (hereinafter sometimes referred to as "GBL") composition and a method for producing the same. In detail, the present invention relates to a GBL composition which when GBL is used as a solvent or a raw material of other products, neither reacts with nor denatures a solute, hardly causes a side-reaction or the like, and is excellent in stability, and to a method for producing the same.

GBL is useful as an industrial solvent or detergent, or a reaction intermediate of polymer chemical products. In addition, GBL is also used as a raw material of N-methylpyrrolidone (hereinafter sometimes referred to as "NMP") that is widely used as a solvent or an electrolytic solution at the time of manufacture of electronic materials or polyvinylpyrrolidone that is widely applied as a water-soluble polymer.

BACKGROUND ART

GBL is industrially produced through hydrogenation reaction of maleic anhydride or succinic anhydride resulting from partial hydrogenation of maleic anhydride, dehydrogenation reaction of 1,4-butanediol, or the like. For example, a method of obtaining GBL through hydrogenation of a succinic acid derivative, such as succinic anhydride, etc., in the presence of a ruthenium-based catalyst; and a method of obtaining GBL through dehydrogenation reaction of 1,4-butanediol are known (Patent Document 1 and Patent Document 4).

However, according to the conventional production method of GBL, it was difficult to remove acid components, for example, organic acids, such as succinic acid, maleic acid, butyric acid, gamma-hydroxybutyric acid, propionic acid, etc., in GBL, and the like, and therefore, there was a limit in application to uses in which GBL is required to be high in purity and neutral as a solvent.

For the purpose of removing such acid components, there is a proposed a method in which an oxide or hydroxide of an alkaline earth metal is added to GBL and thermally treated, followed by distillation (Patent Document 2). In addition, for the same purpose, there is also disclosed a method in which a carbonate of an alkali metal or alkaline earth metal is brought into contact with a crude 5-alkyl-γ-butyrolactone, thereby removing by-produced acid components (Patent Document 3).

BACKGROUND ART DOCUMENT

Patent Document

Patent Document 1: JP-A-64-25771
Patent Document 2: JP-B-7-42279
Patent Document 3: JP-A-2006-143675
Patent Document 4: JP-A-2013-60428

SUMMARY OF INVENTION

Problem that Invention is to Solve

However, according to the foregoing methods, the purification process was complicated, and there was a case where a part of GBL is decomposed with the oxide or hydroxide of an alkaline earth metal to be added or other case.

In order to solve the foregoing problem, the present invention has been made. That is, a problem of the present invention is to provide high-purity GBL capable of preventing occurrence of reaction other than the object at the time of use, which reaction is caused due to a high acidity of GBL. In accordance with the present invention, a high-purity GBL composition with a low acidity and an industrially advantageous production method thereof are provided.

Means for Solving Problem

In order to solve the foregoing problem, the present inventors made extensive and intensive investigations. As a result, it has been found that by allowing a nitrogen-containing compound to exist in a concentration falling within a certain range in a high-purity GBL composition, an acid number of GBL can be kept low, leading to accomplishment of the present invention. In addition, it has been found that in producing a GBL composition, when succinic acid containing a nitrogen-containing compound and/or a derivative thereof is hydrogenated and distilled and purified with a cation exchange resin, GBL with a low acid number containing the above-described prescribed amount of the nitrogen-containing compound can be produced.

Specifically, the gist of the present invention resides in the following [1] to [9].

[1] A gamma-butyrolactone composition, comprising:
gamma-butyrolactone; and
a nitrogen-containing compound,
wherein a content of the gamma-butyrolactone is 99.0% by mass or more, and a total content of the nitrogen-containing compound is 0.1 ppm by mass to 1,000 ppm by mass as converted to a nitrogen atom.

[2] The gamma-butyrolactone composition as described in [1] above,
wherein an acid number is 10 mg-KOH/g or less.

[3] The gamma-butyrolactone composition as described in [1] above,
wherein an acid number is 0.05 to 0.9 mg-KOH/g.

[4] The gamma-butyrolactone composition as described in [1] above,
wherein an acid number is 0.05 to 0.5 mg-KOH/g.

[5] The gamma-butyrolactone composition as described in any one of [1] to [4] above,
wherein a difference between a boiling point at atmospheric pressure of the nitrogen-containing compound and a boiling point at atmospheric pressure of the gamma-butyrolactone is within 50° C.

[6] The gamma-butyrolactone composition as described in any one of [1] to [5] above,
wherein a molecular weight of the nitrogen-containing compound is 1,000 or less.

[7] The gamma-butyrolactone composition as described in any one of [1] to [6] above,
wherein the nitrogen-containing compound is a compound represented by formula (1):

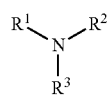

(In the formula (1), $R^1$ to $R^3$ each independently represent a hydrogen atom, an alkyl group, an alkenyl group, an aryl group, an alkoxy group, a hydroxyl group, an amino group, an amide group, an alkylthio group, an arylthio group, an alkylcarbonyl group or an arylcarbonyl group; each of $R^1$ to $R^3$ may further have a substituent; a hetero atom may be contained in the substituent; and two groups selected from $R^1$ to $R^3$ may be bonded to each other to form a ring, provided that a sum total of the carbon atom number of $R^1$ to $R^3$ is 1 or more and 50 or less.)

[8] The gamma-butyrolactone composition as described in any one of [1] to [7] above,
wherein the nitrogen-containing compound is at least one of 2-pyrrolidone and N-methylpyrrolidone.

[9] A method for producing a gamma-butyrolactone composition containing gamma-butyrolactone and a nitrogen-containing compound, in which a content of the gamma-butyrolactone is 99.0% by mass or more, and a total content of the nitrogen-containing compound is 0.1 ppm by mass to 1,000 ppm by mass as converted to a nitrogen atom,
wherein the nitrogen-containing compound is a compound derived from succinic acid or a succinic acid derivative, and
the method comprises the following steps (1) to (3):
Step (1): a step of subjecting succinic acid or a succinic acid derivative to hydrogenation reaction to obtain crude gamma-butyrolactone;
Step (2): a step of distilling the gamma-butyrolactone to distill off a low boiling compound and a high boiling compound; and
Step (3): a step of flowing the gamma-butyrolactone obtained in the step (2) through a cation exchange resin to achieve purification.

Effects of Invention

In accordance with the present invention, it is possible to provide a GBL composition which is low in an acid number, excellent in storage stability, and useful as a solvent, and an industrially advantageous production method thereof.

BRIEF DESCRIPTION OF DRAWING

FIG. 1 is a drawing showing an example of a production process of GBL according to the present invention.

MODE FOR CARRYING OUT INVENTION

Embodiments of the present invention are hereunder described in detail. It should be construed that the present invention is not limited to the following embodiments, and various modifications can be carried out within the scope of the gist.

Here, the terms "% by mass" and "ppm by mass" are synonymous with "% by weight" and "ppm by weight", respectively.

1. γ-Butyrolactone (GBL)

The GBL composition according to the present invention contains 99.0% by mass or more of GBL that is a main component. The GBL content in the GBL composition is more preferably 99.2% by mass or more, and still more preferably 99.5% by mass or more.

In view of the fact that the GBL composition contains a nitrogen-containing compound as described later, an upper limit of the GBL content is less than 100% by mass, preferably 99.995% by mass or less, and more preferably 99.990% by mass or less.

In the present specification, the GBL content is synonymous with a purity of the GBL composition.

1-1. GBL Raw Material

GBL that is the main component of the GBL composition of the present invention is produced by a variety of methods, such as a vapor-phase or liquid-phase catalytic hydrogenation method of maleic acid and/or a maleic acid derivative; a vapor-phase or liquid-phase catalytic hydrogenation method of succinic acid and/or a succinic acid derivative; a dehydrocyclization method of 1,4-butanediol; cyclization of γ-hydroxybutyl aldehyde or γ-hydroxybutyric acid; and the like. The production method is preferably a vapor-phase or liquid-phase catalytic hydrogenation method of maleic acid and/or a maleic acid derivative or a vapor-phase or liquid-phase catalytic hydrogenation method of succinic acid and/or a succinic acid derivative, with the latter being especially preferred.

The term "maleic acid derivative" comprehensively means maleic anhydride and/or maleic ester, fumaric acid, and fumaric ester. In addition, the term "succinic acid derivative" means succinic anhydride and/or a succinic ester, and the succinic acid and/or succinic acid derivative is collectively described as "succinic acid". These raw materials are used solely or as a mixture.

The succinic ester is preferably a linear alkyl ester having 1 to 4 carbon atoms, and especially preferably a dicarboxylic acid dimethyl ester or a dicarboxylic acid diethyl ester. In addition, a salt of the succinic acid can also be used as the raw material for the GBL production. Examples thereof include an ammonium salt, a sodium salt, a potassium salt, a calcium salt, and the like, with an ammonium salt being preferred.

1-2. Succinic Acid Raw Material

As the production method of the succinic acid that is used in the present invention, there is exemplified a method of using a fossil fuel, such as petroleum, etc., as a raw material (hereinafter sometimes referred to as "petrifying method") or a method of producing the succinic acid from biomass resources through a fermentation step (hereinafter sometimes referred to as "bio-method"). Above all, the succinic acid produced by the bio-method is suitably used. The succinic acid produced by the bio-method contains a nitrogen-containing compound, and the GBL composition as prescribed in the present invention can be relatively easily obtained by controlling the concentration of the nitrogen-containing compound within the system in the production and purification steps of GBL.

Examples of the production method of succinic acid by the petrifying method include a method in which a material obtained by subjecting petroleum to fractional distillation by distillation and/or extraction, or a hydrocarbon decomposition product obtained by treating petroleum by catalytic decomposition (for example, fluidization catalytic decomposition, pyrolysis, hydrogenolysis, etc.), is used as the raw material. Examples of the industrial succinic acid raw material include a C4 fraction, a C5 fraction, and a C6 fraction. The succinic acid can be produced directly or via an intermediate from such a succinic acid raw material. Specifically, there can be exemplified a method of producing the succinic acid by oxidizing benzene or butane to produce maleic anhydride or a maleic ester, followed by hydrogenation.

Examples of biomass resources that can be suitably used in the succinic acid production method by the bio-method include plant-derived resources (plant resources), such as wood, paddy straw, chaff, rice bran, old rice, corn, sugar cane, cassava, sago palm, soy pulp, corncobs, tapioca refuse, bagasse, vegetable oil refuse, potatoes, buckwheat, soybeans, fats and oils, old papers, papermaking residues, etc.; animal-derived resources, such as fishery product residues, excreta from domestic animals, etc.; and mixed resources, such as sewage sludge, food wastes, etc. Of those, plant resources are preferred. In addition, among the plant resources, wood, paddy straw, chaff, rice bran, old rice, corn, sugar cane, cassava, sago palm, potatoes, fats and oils, old papers, and papermaking residues are preferred, with corn, sugar cane, cassava, and sago palm being especially preferred.

Examples of carbon sources that are derived from the above-described biomass resources include fermentative carbohydrates, for example, hexoses, such as glucose, mannose, galactose, fructose, sorbose, tagatose, etc.; pentoses, such as arabinose, xylose, ribose, xylulose, ribulose, etc.; di- and polysaccharides, such as maltose, sucrose, lactose, trehalose, starch, cellulose, etc.; fatty acids, such as butyric acid, caproic acid, caprylic acid, capric acid, lauric acid, myristic acid, palmitic acid, palmitoleic acid, stearic acid, oleic acid, linoleic acid, linolenic acid, monocutinic acid, arachidic acid, eicosenoic acid, arachidonic acid, behenic acid, erucic acid, docosapentaenoic acid, docosahexaenoic acid, lignoceric acid, selacholeic acid, etc.; polyalcohols, such as glycerin, mannitol, xylitol, ribitol, etc.; and the like. Among those, hexoses, such as glucose, mannose, galactose, fructose, sorbose, tagatose, etc.; pentoses, such as arabinose, xylose, ribose, xylulose, ribulose, etc.; and di- and polysaccharides, such as maltose, sucrose, lactose, trehalose, starch, cellulose, etc., are preferred, with glucose, maltose, fructose, sucrose, lactose, trehalose, and cellulose being more preferred.

From the foregoing various carbon sources, the succinic acid can be obtained by the fermentation method by means of microbial conversion with coryneform bacteria, *bacillus* bacteria, *rhizobium* bacteria, *mycobacterium*, or the like. As such microorganisms, coryneform bacteria are preferred.

In the microbial conversion by the fermentation method, the reaction temperature and pressure and other reaction conditions depend upon the activity of the microorganism to be selected, such as a bacterial cell, a mold, etc., and may be properly selected according to the object.

There is a case where the succinic acid obtained by the foregoing method contains a nitrogen-containing compound that exists in the biomass, incorporates in the fermentation step, or remains without being fully removed in the purification step of the succinic acid. Such a nitrogen-containing compound can be used as it is as the nitrogen-containing compound of the present invention. In addition, as a method of regulating the content of the nitrogen-containing compound, a general purification method, such as distillation, filtration, crystallization, etc., can be applied.

1-3. High-Purity GBL

Crude GBL is obtained by the foregoing method. The crude GBL contains, in addition to GBL, tetrahydrofuran, succinic anhydride or succinic acid as an intermediate product, or reaction by-products inclusive of an alcohol, such as propanol, butanol, etc., an organic acid, such as propionic acid, butyric acid, enanthic acid, etc., and an ester thereof, high boiling materials, produced water, and the like.

In order to obtain GBL in the GBL composition according to the present invention, it is needed to previously remove a component having a lower boiling point than GBL (a low boiling component or a low boiling compound) from such crude GBL.

As a removal method of the low boiling component, a distillation method is general. For example, a method in which using a twin-column type distillation column, the low boiling component is distilled off in the first column, and subsequently, a GBL product is distilled and obtained in the second column; a method in which using a single-column type distillation column, while distilling off the low boiling component and simultaneously obtaining a GBL product from a side stream, a high boiling material (a high boiling component or a high boiling compound) is separated as a bottom product; and the like are adopted. According to such general methods, it is possible to obtain purified GBL having a purity of 99.0% or more; however, even such high-purity GBL generally has an acid number of 10 mg-KOH/g or more.

1-4. Kind and Concentration of Nitrogen-Containing Compound

In the GBL composition of the present invention, a nitrogen-containing compound is contained in an amount of 0.1 ppm by mass to 1,000 ppm by mass as converted to a nitrogen atom in terms of a total content. In the GBL composition of the present invention, this nitrogen-containing compound may be contained solely or as a mixture of two or more nitrogen-containing compounds.

Though the nitrogen-containing compound that is contained in the GBL composition of the present invention is not particularly limited, a compound represented by the formula (1), an imine compound, or a nitrile compound is preferred, and a compound represented by the following formula (1) is more preferred.

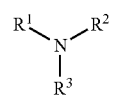

(1)

(In the formula (1), $R^1$ to $R^3$ each independently represent a hydrogen atom, an alkyl group, an alkenyl group, an aryl group, an alkoxy group, a hydroxyl group, an amino group, an amide group, an alkylthio group, an arylthio group, an alkylcarbonyl group or an arylcarbonyl group; these groups may each further have a substituent; a hetero atom may be contained in the substituent; and two groups selected from $R^1$ to $R^3$ may be bonded to each other to form a ring, provided that a sum total of the carbon atom number of $R^1$ to $R^3$ is 1 or more and 50 or less.)

Examples of the imine compound include a compound represented by the following formula (2).

$$R^1R^2C=N-R^3 \quad (2)$$

(In the formula (2), $R^1$ to $R^3$ are each independently synonymous with $R^1$ to $R^3$, respectively in the foregoing formula (1).)

Of those, the compound represented by the formula (2) is preferably a compound having a pyridine ring, a compound having a pyrazole ring, or a compound having a pyrazine ring.

Examples of the nitrile compound include a compound represented by the following formula (3).

$$R^1-C\equiv N \quad (3)$$

(In the formula (3), $R^1$ is synonymous with $R^1$ in the foregoing formula (1).)

1-4-1. Substituents ($R^1$ to $R^3$) in Formulae (1) to (3)

The alkyl group in the substituents ($R^1$ to $R^3$) is a chain (linear or branched) alkyl group or a cyclic alkyl group.

In the case of a chain alkyl group, its carbon atom number is typically 1 to 20, and preferably 1 to 12. Specific examples thereof include a methyl group, an ethyl group, an n-propyl group, an i-propyl group, an n-butyl group, an i-butyl group, a sec-butyl group, a t-butyl group, a pentyl group, a hexyl group, an octyl group, a decyl group, and the like.

In the case of a cyclic alkyl group, its carbon atom number is typically 3 to 20, and preferably 4 to 11. Specific examples thereof include a cyclopentyl group, a cyclohexyl group, a cyclooctyl group, and the like.

The substituent which the alkyl group may have is not particularly limited so long as the effect of the present invention is not conspicuously impaired. Examples thereof include an aryl group, an acyl group, a hydroxyl group, an alkoxy group, an aryloxy group, an alkylaryloxy group, an amino group, an aminoalkyl group, a phosphate group, a phosphono group, a phosphino group, a phosphoryl group, a sulfide group, and the like. Those having a formula weight of about 200 or less are typically used.

The alkenyl group in the substituents ($R^1$ to $R^3$) is a chain (linear or branched) alkenyl group or a cyclic alkenyl group.

In the case of a chain alkenyl group, its carbon atom number is typically 2 to 20, and preferably 2 to 12. Specific examples thereof include an ethenyl group, a 1-propenyl group, an isopropenyl group, a 2-butenyl group, a 1,3-butadienyl group, a 2-pentenyl group, a 2-hexenyl group, and the like.

In the case of a cyclic alkyl group, its carbon atom number is typically 3 to 20, and preferably 4 to 11. Specific examples thereof include a cyclopropenyl group, a cyclopentenyl group, a cyclohexenyl group, and the like.

As the substituent which the alkenyl group may have, the same substituents as those exemplified above for the alkyl group can be used so long as the effect of the present invention is not conspicuously impaired.

Examples of the aryl group in the substituents ($R^1$ to $R^3$) include a phenyl group, a benzyl group, a mesityl group, a naphthyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 2-ethylphenyl group, an isoxazolyl group, an isothiazolyl group, an imidazolyl group, an oxazolyl group, a thiazolyl group, a thiadiazolyl group, a thienyl group, a thiophenyl group, a triazolyl group, a tetrazolyl group, a pyridyl group, a pyrazinyl group, a pyrimidinyl group, a pyridazinyl group, a pyrazolyl group, a pyrrolyl group, a pyranyl group, a furyl group, a furazanyl group, an imidazolidinyl group, an isoquinolyl group, an isoindolyl group, an indolyl group, a quinolyl group, a pyridothiazolyl group, a benzimidazolyl group, a benzoxazolyl group, a benzothiazolyl group, a benzotriazolyl group, a benzofuranyl group, an imidazopyridinyl group, a triazopyridinyl group, a purinyl group, and the like. The carbon number thereof is typically 5 to 20, and preferably 5 to 12. These groups include heteroaryl groups containing an oxygen atom, a nitrogen atom, a sulfur atom, or the like.

The substituent which the aryl group may have is not particularly limited so long as the effect of the present invention is not conspicuously impaired. Examples thereof include an alkyl group having 1 to 10 carbon atoms, an acyl group having 1 to 10 carbon atoms, an alkoxy group having 1 to 10 carbon atoms, a cycloalkyl group having 1 to 10 carbon atoms, an aryl group having 6 to 10 carbon atoms, an aryloxy group having 6 to 10 carbon atoms, an alkylaryl group having 7 to 12 carbon atoms, an alkylaryloxy group having 7 to 12 carbon atoms, an arylalkyl group having 7 to 12 carbon atoms, an arylalkoxy group having 7 to 12 carbon atoms, a hydroxyl group, and the like. In addition, in such a substituent, a hetero atom, such as an oxygen atom, a nitrogen atom, a sulfur atom, a phosphorus atom, etc., may be contained.

The carbon atom number of the alkyl group moiety of the alkoxy group in the substituents ($R^1$ to $R^3$) is typically 1 to 20, and preferably 1 to 12. Specific examples of the alkoxy group include a methoxy group, an ethoxy group, a butoxy group, a phenoxy group, and the like. As the substituent which the alkoxy group may have, the same substituents as those exemplified above for the alkyl group can be used so long as the effect of the present invention is not conspicuously impaired.

As the amino group in the substituents ($R^1$ to $R^3$), its carbon atom number is typically 0 to 20, and preferably 0 to 12. Specific examples thereof include an amino group ($-NH_2$), a methylamino group, an ethylamino group, a propylamino group, a butylamino group, a dimethylamino group, a diethylamino group, an anilino group, a toluidino group, an anisidino group, a diphenylamino group, an N-methyl-N-phenylamino group, and the like. As the substituent which the amino group may have, the same substituents as those exemplified above for the alkyl group can be used so long as the effect of the present invention is not conspicuously impaired.

The carbon atom number of the alkyl group moiety of the alkylthio group in the substituents ($R^1$ to $R^3$) is typically 1 to 20, and preferably 1 to 12. Specific examples of the alkylthio group include a methylthio group, an ethylthio group, a propylthio group, an isopropylthio group, and the like. As the substituent which the alkylthio group may have, the same substituents as those exemplified above for the alkyl group can be used so long as the effect of the present invention is not conspicuously impaired.

The carbon atom number of the aryl group moiety of the arylthio group in the substituents ($R^1$ to $R^3$) is typically 6 to 20, and preferably 6 to 12. Specific examples of the arylthio group include a phenylthio group, a tolylthio group, and the like. As the substituent which the arylthio group may have, the same substituents as those exemplified above for the alkyl group can be used so long as the effect of the present invention is not conspicuously impaired.

The carbon atom number of the alkyl group moiety or aryl group moiety of the alkylcarbonyl group or arylcarbonyl group in the substituents ($R^1$ to $R^3$) is typically 0 to 20, and preferably 0 to 12. In the case where at least one of the substituents ($R^1$ to $R^3$) is an alkylcarbonyl group or an arylcarbonyl group, the compound represented by the formula (1) becomes an alkylamide or an arylamide as a whole. The explanation is hereinafter made while referring the foregoing alkylamide or arylamide as an amide compound.

The amide group in the amide compound generally has a resonance structure, and an unpaired electron on the nitrogen atom is delocalized by the adjacent carbonyl group. Therefore, the amide is in general weak in basicity, and even when coexisting with GBL, it hardly causes a side reaction.

In the case where the compound represented by the formula (1) has two alkylcarbonyl groups and/or arylcarbonyl groups as the substituents ($R^1$ to $R^3$) of the foregoing nitrogen atom, the compound becomes an imide compound. In the present specification, the amide compound includes an imide compound, too.

In the case of the amide compound and the imide compound, among the substituents bonding to the nitrogen atom in the formula (1), the number of substituent or substituents other than the alkylcarbonyl group or arylcarbonyl group is 1 or 2. As the one or two substituents, those used for $R^1$ to $R^3$ as described above are used without being particularly limited. The preferred substituent is an alkyl group, an alkenyl group or an aryl group.

1-4-2. Nitrogen-Containing Compound

Though a molecular weight of the nitrogen-containing compound is not particularly limited, it is preferably 1,000 or less. When the molecular weight of the nitrogen-containing compound is high as more than 1,000, the compatibility with GBL tends to become low, and there is a possibility that the nitrogen-containing compound is separated during the storage, or when the temperature is low, it is deposited. The molecular weight is preferably 500 or less, and more preferably 300 or less.

When the molecular weight of the nitrogen-containing compound falls within the foregoing range, the nitrogen content is readily regulated, and the stability during the storage becomes good. The molecular weight can be measured by, for example, a gas chromatograph molecular weight meter or the like.

Among nitrogen-containing compounds, specific examples of the nitrogen-containing compound represented by the foregoing formula (1) include amides having a chain skeleton, such as octylamine, nonylamine, 1-aminodecane, aniline, phenethylamine, dipentylamine, dihexylamine, diheptylamine, N-methylaniline, tributylamine, tripentylamine, trihexylamine, triheptylamine, trioctylamine, N,N-dimethylaniline, dicyclohexylamine, 1,3-propanediamine, N,N-dimethyl-1,6-hexanediamine, N-butylpyrrole, N-butyl-2,3-dihydropyrrole, N-butylpyrrolidine, 4-dimethylaminopyridine, 1,2,3,4-tetrahydroquinoline, 2,3-dihydro-1H-indole, 4-aminomethylpiperidine, 4-amino-5,6-dihydro-2-methylpyrimidine, 2,3,5,6-tetramethylpyrazine, 3,6-dimethylpyridazine, acetamide, N-methylacetamide, N-ethylacetamide, N,N-dimethylacetamide, succinic acid monoamide, succinic acid diamide, etc.; aromatic amides, such as benzamide, etc.; cyclic amides, such as 2-pyrrolidone (hereinafter sometimes referred to as "2P"), N-methylpyrrolidone, N-ethylpyrrolidone, N-vinylpyrrolidone, 2-piperidone, N-methylpiperidone, etc.; and imides, such as succinic acid imide, N-methylsuccinic acid imide, etc.

Of those, secondary amines or tertiary amines, such as tributylamine, tripentylamine, trihexylamine, triheptylamine, trioctylamine, N-butyl-2,3-dihydropyrrole, etc.; and amides, such as succinic acid diamide, succinic acid monoamide, acetamide, 2-pyrrolidone, N-methylpyrrolidone, succinic acid imide, N-methylsuccinic acid imide, etc., are preferred compounds. Of those, 2-pyrrolidone and N-methylpyrrolidone are preferred, with N-methylpyrrolidone being especially preferred.

Among nitrogen-containing compounds, specific examples of the nitrogen-containing compound represented by the foregoing formula (2) include imidazole, oxazole, ethyl isocyanate, pyridine, pyrazole, pyrimidine, 1-methylimidazole, 4-methylimidazole, propyl isocyanate, methylpyridine, methylpyrimidine, methylpyrazine, 2,3,5,6-tetramethylpyrazine, 3,6-dimethylpyridazine, tetramethylpyrazole, 3,6-dimethylpyridazine, and the like.

Among nitrogen-containing compounds, specific examples of the nitrogen-containing compound represented by the foregoing formula (3) include acetonitrile, acrylonitrile, propionitrile, glycolonitrile, butyronitrile, cyanobutadiene, succinonitrile, valeronitrile, isovaleronitrile, benzonitrile, and the like.

Though a boiling point of the nitrogen-containing compound contained in the GBL composition of the present invention is not particularly limited, a difference between a boiling point at atmospheric pressure of at least one nitrogen-containing compound contained in the GBL composition and a boiling point at atmospheric pressure of GBL is preferably within 50° C., and more preferably within 30° C.

Similarly, a relative volatility at 200° C. and at atmospheric pressure between at least one nitrogen-containing compound contained in the GBL composition and GBL is preferably 10 or less, and more preferably 5 or less.

By allowing the boiling point difference between the nitrogen-containing compound and GBL and/or the relative volatility to fall within the foregoing range, even when the GBL composition is used as a solvent or an electrolytic solution, etc. that is a main application, an evaporation loss of the nitrogen-containing compound in the composition can be reduced, and the generation of a side reaction due to an increase of acidity of the GBL composition can be inhibited. Also, remaining of the nitrogen-containing compound in distillation after use of the GBL composition can be lessened, so that an adverse influence against the post-process is suppressed.

The boiling point at atmospheric pressure of every representative nitrogen-containing compound is shown in Table 1. In addition, the relative volatility at 200° C. and at atmospheric pressure between every representative nitrogen-containing compound and gamma-butyrolactone is shown in Table 2.

TABLE 1

| Compound | Boiling point (° C.) |
| --- | --- |
| Monomethylamine | −21 |
| Dimethylamine | 6.1 |
| Trimethylamine | 2.8 |
| NMP | 202 |
| GBL | 204 |
| Acetamide | 221 |
| N-Methylsuccinic acid imide | 234 |
| 2-Pyrrolidone | 251 |
| Succinic acid imide | 281 |
| Succinic acid monoamide | 421 |
| Succinic acid diamide | 494 |

The boiling points of succinic acid monoamide and succinic acid diamide are a calculated value.

TABLE 2

| | Relative volatility at 200° C. to GBL |
| --- | --- |
| 2-Pyrrolidone | 3.7 |
| NMP | 1.0 |
| Monomethylamine | 148.6 |
| Dimethylamine | 545.8 |
| Trimethylamine | 149.0 |
| Succinic acid imide | 14.9 |
| Acetamide | 1.6 |
| Succinic acid diamide | >20 |

1-5. Effect of Nitrogen-Containing Compound

In the present invention, a total content (concentration) of the nitrogen-containing compound relative to the GBL composition is 0.1 ppm by mass to 1,000 ppm by mass as converted to a nitrogen atom. By allowing the nitrogen-containing compound to be contained in such a ratio in the GBL composition, a stable GBL composition can be obtained. Though the reason for this is not elucidated yet, the following may be conjectured.

That is, the nitrogen-containing compound neutralizes acidic impurities, such as succinic acid, gamma-hydroxybutyric acid, etc., in the GBL composition. However, so long as the nitrogen-containing compound that is used in the GBL composition of the present invention is contained in an amount of 0.1 ppm by mass to 1,000 ppm by mass, a range of which is the prescribed scope in the present application, it is chemically stable and hardly reacts with the components in the GBL composition. In addition, the nitrogen-containing compound that is used in the present invention is neutral to weakly basic, and so long as it is contained in an amount of 0.1 ppm by mass to 1,000 ppm by mass, a range of which is the prescribed scope in the present application, as compared with strong bases, for example, metal hydroxides, etc., it neither denatures nor deteriorates GBL and does not adversely affect stability of the GBL composition.

When the total concentration of the nitrogen-containing compound in the GBL composition exceeds 1,000 ppm by mass as converted to a nitrogen atom and becomes high, the GBL composition exhibits basicity, GBL is readily decomposed, and impurities likely causing coloration are readily produced. Though a degree of coloration can be judged by an absorbance, the absorbance can be measured using a spectrophotometer.

The coloration is caused due to formation of a carbonyl compound or an unsaturated bond, or polymerization of GBL or the nitrogen-containing compound. When the nitrogen-containing compound is contained in a concentration more than the prescribed concentration in the present application, there is a tendency that such formation of a carbonyl compound or an unsaturated bond or polymerization is remarkably promoted. In general, though a high-purity GBL composition is substantially free from light absorption in a wavelength region of more than 250 nm, when the above-described formation of a carbonyl compound or an unsaturated bond or polymerization, or the like is caused, there is a tendency that the light absorption increases in a wavelength region of more than 250 nm, especially at 260 nm.

In addition, when the total concentration of the nitrogen-containing compound is low as less than 0.1 ppm by mass as converted to a nitrogen atom, there is a case where an effect for neutralizing an acidic component, for example, succinic acid, butyric acid, propionic acid, or the like, in the GBL composition is not thoroughly obtained. In addition, there is a case where in view of the fact that the proportion of the nitrogen-containing compound having a high dielectric constant and having ability as an electrical carrier in the GBL composition is extremely low, the electrical conductance becomes low. By allowing the concentration of the nitrogen-containing compound in the GBL composition to fall within the scope of the present invention, it is possible to provide a GBL composition that is substantially neutral and low in acid number, in which GBL is hardly decomposed, and that is useful as a solvent, a raw material of chemical products, an electrolytic solution, and so on.

1-6. Control Method of Content of Nitrogen-Containing Compound in GBL Composition As described previously, the content of the nitrogen-containing compound, as converted to a nitrogen atom, in the GBL composition (hereinafter sometimes referred to as "nitrogen atom content") is 0.1 ppm by mass or more and 1,000 ppm by mass or less, preferably 0.2 ppm by mass or more and 500 ppm by mass or less, and more preferably 0.5 ppm by mass or more and 100 ppm by mass or less.

The nitrogen atom content in the GBL composition can be measured by means of gas chromatography or using a GC-MS analyzer combining this with a mass spectrometer, a nitrogen content analyzer using a combustion/chemical vacuum luminescence method, or the like.

Though a method of controlling the nitrogen atom content in the GBL composition is not particularly limited, it is preferred to control the nitrogen atom content by a step of purifying the raw material succinic acid and/or purifying crude GBL, and above all, it is especially preferred to control the nitrogen atom content by a step of purifying crude GBL.

In the case where the nitrogen atom content in the GBL composition is more than the scope of the present invention, it is possible to control the nitrogen atom content in the GBL composition to the concentration in the present invention by, for example, a method of mixing a succinic acid raw material having a low nitrogen atom content or a succinic acid raw material not containing the nitrogen-containing compound at all; a method of separating and removing the nitrogen-containing compound by distillation or the like; a method of adsorbing and separating with a cation exchange resin; a method of diluting with a GBL composition having a low content of the nitrogen-containing compound; or the like.

In addition, in the case where the nitrogen atom content in the GBL composition is lower than the scope of the present application, for example, a method of using a succinic acid raw material having a high nitrogen atom content; a method of adding the nitrogen-containing compound in a GBL production process; a method of decreasing a discharge proportion of the nitrogen-containing compound in a purification step of crude GBL by distillation or cation exchange resin treatment; a method of adding the nitrogen-containing compound directly in the purified GBL composition; or the like may be adopted.

1-7. Acid Number

The matter that the acid number is low is one of the characteristic features of the GBL composition of the present invention. The acid number can be measured by the neutral titration method with a potassium hydroxide aqueous solution or the like as in JIS K0070-1992.

The acid number in the GBL composition of the present invention is typically 10 mg-KOH/g or less, preferably 0.05 to 0.9 mg-KOH/g, and more preferably 0.05 to 0.5 mg-KOH/g. When the acid number is excessively high, there is a case where the reactivity of the GBL composition increases, thereby advancing other reaction than the desired reaction, or GBL is decomposed and/or polymerized, so that coloration or the like is liable to be caused. In addition, though a lower limit value of the acid number is not particularly prescribed, if it is contemplated to make the acid number in the GBL composition excessively low, the purification step becomes complicated, or the additive amount of the basic component increases, whereby GBL is liable to be decomposed and/or polymerized.

In addition, by allowing the acid number of the GBL composition to fall within the predetermined range of the present invention, good electrical conductivity is obtained. Therefore, the GBL composition of the present invention is especially useful as an application requiring electrical conductivity and chemical stability in an electrical conduction band, such as an electrolytic solution, etc.

2. GBL Production Process

As described previously, the GBL composition of the present invention can be suitably produced through hydrogenation of the succinic acid. That is, the method for producing the gamma-butyrolactone composition according to the present invention comprises the following steps (1) to (3). In addition, the gamma-butyrolactone composition obtained by the foregoing production method contains gamma-butyrolactone and a nitrogen-containing compound, in which a content of the gamma-butyrolactone is 99.0% by mass or more, a total content of the nitrogen-containing compound is 0.1 ppm by mass to 1,000 ppm by mass as converted to a nitrogen atom, and the nitrogen-containing compound is a compound derived from succinic acid or a succinic acid derivative.

Step (1): a step of subjecting succinic acid or a succinic acid derivative to hydrogenation reaction to obtain crude gamma-butyrolactone;

Step (2): a step of distilling the gamma-butyrolactone to distill off a low boiling compound and a high boiling compound; and Step (3): a step of flowing the gamma-butyrolactone obtained in the step (2) through a cation exchange resin to achieve purification.

This method is hereunder simply described.

2-1. Purification of Succinic Acid

The succinic acid that is used for the production of GBL as the raw material of the GBL composition may be a succinic acid produced by any method of the petrifying method and the bio-method, and those succinic acids may be used solely or as a mixture.

The purity of such a raw material succinic acid is preferably higher from the standpoint of reaction efficiency, and hence, it is desirable that a crude product to which some purification has been applied is subjected to the reaction.

The crude succinic acid obtained by any method of the petrifying method and the bio-method can also be separated and purified from the reaction liquid according to the usual method.

However, in general, the bio-method is frequently accompanied by a wide variety of by-products, and therefore, it is possible to obtain a high-purity succinic acid by subjecting a culture solution to centrifugation, filtration, or the like to remove a solid, such as a bacterial cell, etc., then desalting the resultant with an ion exchange resin or the like, and subjecting the resulting solution to crystallization or column chromatography.

2-2. Hydrogenation Reaction of Succinic Acid 2-2-1. Catalyst

A hydrogenation catalyst that can be used for the hydrogenation reaction of a succinic acid is preferably one containing at least one metal selected from transition metals belonging to the Groups 8 to 11 of the Periodic Table. Examples of the transition metals belonging to the Groups 8 to 11 of the Periodic Table include iron, ruthenium, osmium, cobalt, rhodium, iridium, nickel, palladium, platinum, copper, silver, gold, and the like. From the standpoint of catalytic activity, ruthenium, copper, and palladium are preferred, and copper and ruthenium with high catalytic activity are especially preferred. A form of the catalyst may be any of a solid catalyst and a complex catalyst; however, in order to obtain a GBL composition with a higher quality, a complex catalyst is preferred.

2-2-2. Solid Catalyst

As for the solid catalyst, a compound containing the above-described metal may be used as it is, or a material having the metal supported on a cattier may also be used.

In the case of using a carrier, the carrier is preferably carbon, alumina, silica, silica-alumina, silica-titania, titania, titania-alumina, barium sulfate, calcium carbonate, or strontium carbonate, and a combination thereof may also be used. A shape of the carrier is a powder, a granule, a pellet, or the like, and is not particularly limited. Use of the carrier is efficient and preferred because odoriferous components or coloring components or organic impurities in the raw material succinic acid can be simultaneously adsorbed and removed. A supporting amount of the metal is typically 0.1 to 10% by weight of the carrier.

As for such a supported catalyst, one in which at least one selected from the group consisting of copper oxide, palladium, platinum, iridium, rhodium, nickel, rhenium, and ruthenium is used as the metal component, and alumina, silica, carbon, or titanium is arbitrarily combined with each metal component may be chosen taking into consideration use conditions or strength.

Preferred examples of the supported catalyst include alumina-supported iron oxide, silica-supported copper oxide, carbon-supported ruthenium, alumina-supported ruthenium, carbon-supported palladium, alumina-supported palladium, titania-supported palladium, carbon-supported platinum, alumina-supported platinum, carbon-supported rhodium, alumina-supported rhodium, and the like.

2-2-3. Complex Catalyst

The complex catalyst is formed of a catalyst metal and a ligand coordinating thereto.

The complex catalyst is hereunder described with reference to a complex catalyst using ruthenium as a metal component as an example.

As a raw material of the metal component, all of metallic ruthenium and a ruthenium compound can be used.

As the ruthenium compound, an oxide, a hydroxide, an inorganic acid salt, an organic acid salt, a complex compound, and the like can be used. Examples thereof include ruthenium oxides, ruthenium hydroxides, or ruthenium salts, such as ruthenium dioxide, ruthenium tetroxide, ruthenium dihydroxide, ruthenium chloride, ruthenium bromide, ruthenium iodide, ruthenium nitrate, ruthenium acetate, etc.; salts of ruthenic acid, such as sodium hexachlororuthenate, dipotassium tetracarbonylruthenate, dicesium octadecacarbonylhexaruthenate, tetraphenylphosphonium undecacarbonylhydridetriruthenate, etc.; ruthenium complexes, such as pentacarbonylruthenium, tris(acetylacetonato)ruthenium, cyclopentadienyldicarbonylruthenium, dibromotricarbonylruthenium, chlorotris(triphenylphosphine)hydrideruthenium, tetra(triphenylphosphine)dihydrideruthenium, tetra(trimethylphosphine)dihydrideruthenium, bis(tri-n-butylphosphine)tricarbonylruthenium, tetrahydridedodecacarbonyltetraruthenium, dodecacarbonyltriruthenium, etc.; and the like. Above all, in view of the fact that those having a high purity are readily available, ruthenium chloride, tris(acetylacetonato)ruthenium, and ruthenium acetate are preferably used.

The ligand of the ruthenium complex catalyst that is used for hydrogenation of the succinic acid is preferably a phosphorus ligand. As the phosphorus ligand, though one having an aryl group, such as triphenylphosphine, diphenylmethylphosphine, dimethylphenylphosphine, etc., can be used, a trialkylphosphine, especially a trialkylphosphine in which a phosphorus atom is bonded to a primary alkyl group, or a decomposition product thereof, is preferred. This alkyl group may have other substituent.

The carbon number of the alkyl group of such a trialkylphosphine is preferably about 1 to 12, and all of the three alkyl groups are not necessarily identical. All of the alkyl groups may be the same as or different from each other, and two of them may are the same, with the other one being different.

Examples of the phosphine capable of forming a ligand include phosphines, such as tridecanylphosphine, trinonylphosphine, trioctylphosphine, triheptylphosphine, trihexylphosphine, tripentylphosphine, tributylphosphine, tripropylphosphine, triethylphosphine, trimethylphosphine, dimethyloctylphosphine, dioctylmethylphosphine, dimethylheptylphosphine, diheptylmethylphosphine, dimethylhexylphosphine, dihexylmethylphosphine, dimethylcyclohexylphosphine, dicyclohexylmethylphosphine, dimethylpentylphosphine, dipentylmethylphosphine, dimethylbutylphosphine, dibutylmethylphosphine, triheptylphosphine, tricyclohexylphosphine, trihexylphosphine, tripentylphosphine, tribenzylphosphine, 1,1,2,2-dimethylphosphinoethane, 1,1,2,2-dimethylphosphinopropane, 1,1,2,2-dimethylphosphinobutane, 1,1,2,2-dioctylphosphinoethane, 1,1,2,2-dioctylphosphinopropane, 1,1,2,2-dioctylphosphinobutane, 1,1,2,2-dihexylphosphinoethane, 1,1,2,2-dihexylphosphinopropane, 1,1,2,2-dihexylphosphinobutane, 1,1,2,2-dibutylphosphinoethane, 1,1,2,2-dibutylphosphinopropane, 1,1,2,2-dibutylphosphinobutane, 1,1-diphosphinane, 1,4-dimethyl-1,4-diphosphane, 1,3-dimethylphospholinane, 1,4-dimethylphospholinane, 8-methyl-8-phosphinobicyclooctane, 4-methyl-4-phosphatetracyclooctane, 1-methylphosphorane, 1-methylphosphonane, etc. As for a shape thereof, all of a monodentate ligand, a multidentate ligand, and a cyclic ligand are useful.

In addition, as the phosphorus ligand, not only the above-described phosphines but also, for example, a phosphite, a phosphinate, a phosphine oxide, an amino phosphine, a phosphinic acid, and the like can be used.

A use amount of such a phosphorus ligand is in the range of from 0.1 to 1,000 mols, and preferably 1 to 100 mols per mol of the ruthenium metal.

In addition, what the ruthenium complex catalyst for hydrogenation of the succinic acid is used for the reaction in a form of a cationic complex with a conjugated base of an acid having a pKa of smaller than 2 is preferred from plural standpoints of an improvement of the activity, stability of the catalyst, and the like.

As for the conjugated base of an acid having a pKa of small than 2, any material capable of forming such a conjugated base at the time of catalyst preparation or in the reaction system may be used, and for example, a Brønsted acid having a pKa of smaller than 2 or a variety of salts thereof, or the like is useful.

Examples of the acid or its salt capable of being used for such an object include Brønsted acids of an inorganic acid, such as nitric acid, perchloric acid, fluoroboric acid, hexafluorophosphoric acid, fluorosulfonic acid, etc., or an organic acid, such as trichloroacetic acid, dichloroacetic acid, trifluoroacetic acid, dodecylsulfonic acid, octadecylsulfonic acid, trifluoromethanesulfonic acid, benzenesulfonic acid, p-toluenesulfonic acid, tetra(pentafluorophenyl) boric acid, a styrene sulfonate-divinylbenzene copolymer, etc.; and salts of these acids, such as an alkali metal salt, an alkaline earth metal slat, an ammonium salt, a silver salt, etc.

In addition, such an acid or salt may also be added in a form of an acid derivative in which the above-described conjugated base of an acid is considered to be formed in the reaction system. For example, even when the acid or its salt is added in a form of an acid halide, an acid anhydride, an ester, an acid amide, or the like in the reaction system, the same effect is expected to be brought.

A use amount of such an acid or salt thereof is 1,000 mols or less, preferably 100 mols or less, and more preferably 10 mols or less relative to the ruthenium metal.

2-2-4. Solvent

Though the hydrogenation of the succinic acid can be carried out using a mixture of the reaction raw material and reaction production as a solvent, a variety of solvents can be used within the range where the purpose and progress of the reaction are not impaired.

Examples of such a solvent include ethers, such as diethyl ether, anisole, tetrahydrofuran, ethylene glycol dimethyl ether, dioxane, etc.; alcohols, such as methanol, ethanol, n-butanol, benzyl alcohol, phenol, ethylene glycol, diethylene glycol, etc.; carboxylic acids, such as formic acid, acetic acid, propionic acid, toluic acid, etc.; esters, such as methyl acetate, butyl acetate, benzyl benzoate, etc.; aromatic hydrocarbons, such as benzene, toluene, ethylbenzene, tetralin, etc.; aliphatic hydrocarbons, such as n-hexane, n-octane, cyclohexane, etc.; halogenated hydrocarbons, such as dichloromethane, trichloroethane, chlorobenzene, etc.; nitro compounds, such as nitromethane, nitrobenzene, etc.; carboxylic acid amides, such as N,N-dimethylformamide, N,N-dimethylacetamide, N-methylpyrrolidone, etc.; hexamethylphosphoric triamide and other amides; ureas, such as N,N-dimethylimidazolidinone, etc.; sulfones, such as dimethylsulfone, etc.; sulfoxides, such as dimethyl sulfoxide, etc.; lactones, such as caprolactone, etc.; polyethers, such as tetraglyme, triglyme, etc.; carbonic acid esters, such as dimethyl carbonate, ethylene carbonate, etc.; and the like, with ethers, polyethers, and lactones being preferred.

2-2-5. Reaction Conditions

As for the hydrogenation reaction of the succinic acid, any of continuous and batchwise modes can be adopted. A reaction temperature is typically 50 to 250° C., preferably 100 to 250° C., and more preferably 150 to 220° C. Though a hydrogen partial pressure within the reaction system is not particularly limited, it is typically 0.01 to 10 MPa·G (gauge pressure), and preferably 0.03 to 5 MPa·G from the industrial standpoint.

From the reaction product liquid, GBL that is the desired product can be separated by usual separation means, such as distillation, extraction, etc.

A moisture content within the reaction system is preferably 0.01 to 5% by mass, and more preferably 0.1 to 1% by mass. When the moisture content is excessively high, the equilibrium between a succinic acid and its anhydride is shifted to the succinic acid side, and therefore, the concentration of the succinic anhydride becomes low, so that a formation rate of GBL tends to be lowered. On the other hand, when the moisture content is excessively low, the concentration of the succinic acid serving as a counter anion of the ruthenium catalyst is lowered, and the cationic properties of the catalyst are lowered, so that the hydrogenation reaction activity of the catalyst tends to be lowered.

As a method of removing the moisture from the reaction system, a gas stripping method and the like can be adopted, and moisture removal by distillation or addition of a dehydrating agent may be performed depending upon the reaction process. When hydrogen is used as the gas for gas stripping, conversion of the succinic acid to GBL can be achieved simultaneously with the removal of moisture in the reaction liquid, and hence, such is efficient.

2-3. Purification of Crude GBL

From the crude GBL obtained by the above-described reaction, high-purity purified GBL can be obtained by a general purification method, such as extraction, distillation, crystallization, etc.

An outline of the purification method of crude GBL is hereunder described. However, it should be construed that the order of these steps, a mode, such as a batchwise or continuous mode, etc., a form of individual treatment facilities, and so on are not limited by the following description so long as the gist of the present invention is not deviated.

2-3-1. Distillation Step

The separation and purification of the desired product from the reaction liquid or reaction mixture can be performed by the usual method using a distillation method, and a vacuum distillation method may be adopted depending upon the kind of the solvent used for the reaction.

In the reaction mixture, besides GBL that is the desired product, a high boiling component (high boiling compound), such as the unreacted succinic acid component, the catalyst, the solvent, and the like, and a low boiling component (low boiling compound), such as impurities in the raw material, by-products formed during the reaction, etc., are contained. Therefore, these materials are removed by means of distillation. In addition, though the nitrogen-containing compound in the crude GBL can be separated by means of distillation, it is generally difficult to separate a nitrogen-containing compound having a boiling point close to GBL.

As for the above-described distillation, it is possible to adopt a method of using a single multistage distillation column and drawing out GBL from a middle stage of the distillation column; however, in general, from the standpoints of stability of the driving operation and column height of the distillation column and from other reasons, it is preferred to perform the distillation operation using plural distillation columns, preferably two distillation columns. The distillation operation is hereunder described with reference to the case of using two distillation columns as an example.

(First Distillation Column)

A purification step is hereunder described with reference to a process shown in FIG. 1 as an example.

In FIG. 1, in a first distillation column, a component having a higher boiling point than GBL (high boiling compound), inclusive of an unreacted succinic acid, a catalyst, a solvent, and the like, is removed from a reaction mixture taken out from a reactor. The catalyst, the unreacted succinic acid, the solvent, and the like contained in this high boiling component may be circulated as they are into the reaction step.

The component containing GBL as taken out from the column top of the first distillation column is fed into a second distillation column.

A theoretical stage number is preferably 3 stages or more and 100 stages or less, and more preferably 5 stages or more and 50 stages or less. When the theoretical stage number is excessively small, the purity of GBL as the desired product tends to be lowered. When the theoretical stage number is excessively large, the amount of heat necessary for distillation increases, and the column height of the distillation column becomes high, so that such is not economical.

Though a reflux ratio can be adjusted according to the purity of the desired purified GBL, in general, it is preferably 0.01 or more and 100 or less, and more preferably 0.1 or more and 50 or less.

A column top pressure is preferably 1 kPa or more and 200 kPa or less, more preferably 2 kPa or more and 100 kPa or less, and still more preferably 5 kPa or more and 50 kPa or less in terms of an absolute pressure.

A temperature of the column bottom is preferably 50° C. or higher and 300° C. or lower, more preferably 100° C. or higher and 250° C. or lower, and especially preferably 120° C. or higher and 230° C. or lower.

When the column top pressure is excessively high, or the temperature of the column bottom is excessively low, the distillation of GBL as the desired product becomes insufficient, so that the yield tends to be lowered. Conversely, when the column top pressure is excessively low, or the temperature of the column bottom is excessively high, not only the purity of the obtained purified GBL is lowered, but also denaturation of the hydrogenation catalyst, or decomposition and heat generation of sugars contained as an unreacted raw material, possibly occurs, so that there is a case where the stability of the process is lowered.

(Second Distillation Column)

Though a distillate obtained in the above-described first distillation column may be productized as it is as purified GBL, as shown in FIG. 1, it is preferred to further purify the distillate in a second distillation column for removing a component having a lower boiling point than GBL (low boiling compound).

Though a site at which GBL is drawn out from the second distillation column is not particularly limited, the raw material to be fed into the second distillation column is crude GBL from which the high boiling component has been removed in the first distillation column, and therefore, it is general to recover GBL from the column bottom.

A theoretical stage number of the second distillation column may be chosen from the same range as in the first distillation column so long as no particular reason exists. In addition, the reflux ratio and the operation pressure in the second distillation column are the same as those in the first distillation column.

A column bottom temperature of the second distillation column is preferably 20° C. or higher and 250° C. or lower, more preferably 50° C. or higher and 230° C. or lower, and especially preferably 80° C. or higher and 200° C. or lower.

While illustration is omitted in FIG. 1, GBL recovered from the second distillation column may be further distilled.

Though the distillation operation in these distillation columns may be either a batchwise mode or a continuous mode, continuous distillation is preferred from the viewpoint of productivity. Though a mode of the distillation may be either simple distillation or multistage distillation, it is preferably multistage distillation from the viewpoint of separation performance. As for a form of the distillation column, all of a plate column and a packed column packed with regular and/or irregular packings are useful.

2-3-2. Cation Exchange Treatment Step

Though GBL recovered from the column bottom of the second distillation column may be used as it is as a product, it is preferred to flow the resulting GBL through a column filled with a cation exchange resin, thereby achieving removal of ions or basic impurities and purification. As the cation exchange resin, all of a strongly acidic cation exchange resin and a weakly acidic cation exchange resin can be used, and a shape thereof may be either a gel type or a porous type. From the standpoint of efficiency of ion exchange, a strongly acidic cation exchange resin having high strength as an acid is preferred.

Although the reaction production liquid may be made subjective to the treatment with a cation exchange resin, in general, it is efficient to make the GBL composition after separating the catalyst, the unreacted succinic acid, the solvent, and the like by means of distillation or the like subjective to the treatment. In particular, it is most preferred to treat the GBL composition after separation of GBL and water.

The treatment with an ion exchange resin may be either a batchwise mode or a continuous flow mode. A treatment temperature is typically 0° C. to 100° C., and a treatment time may be several minutes to several tens hours. Though a treatment pressure is generally 10 kPa to 1,000 kPa in terms of an absolute pressure, the treatment may also be performed under reduced pressure.

A treatment speed is typically about 0.1 to 10 hours$^{-1}$ in terms of a spatial velocity (SV). When the spatial velocity is excessively large, there is a case where a pressure loss before and after the column becomes large, or the impurities cannot be sufficiently removed. On the other hand, when the spatial velocity is excessively small, there is a case where the column becomes excessively large, or the treatment speed becomes slow.

2-3-3. Catalyst Circulation Step

As shown in FIG. 1, in the present invention, it is preferred to circulate the catalyst or catalyst liquid containing the unreacted succinic acid drawn out from the first distillation column into the reaction step. This circulated liquid may contain, in addition to the above-described active component, the solvent and other components so long as the reaction step is not adversely affected. For example, in FIG. 1, at least a part of the high boiling component containing the unreacted succinic acid, as separated from GBL and other low boiling component in the first distillation column is circulated into the reaction step.

EXAMPLES

The present invention is hereunder described in more detail with reference to Examples, but it should be construed that the present invention is not limited by the following Examples so long as the gist of the present invention is not deviated.

All of "ppm" in the following Examples mean "ppm by mass".

1. Raw Materials

γ-Butyrolactone (GBL): Special grade chemical (manufactured by Wako Pure Chemical Industries, Ltd.)
2-Pyrrolidone (2P): Special grade chemical (manufactured by Wako Pure Chemical Industries, Ltd.)
N-Methylpyrrolidone (NMP): Special grade chemical (manufactured by Wako Pure Chemical Industries, Ltd.)
Succinic acid diamide: Special grade chemical (manufactured by Wako Pure Chemical Industries, Ltd.)
Potassium hydroxide: Special grade chemical (manufactured by Wako Pure Chemical Industries, Ltd.)
Fumaric acid (FMS): Special grade chemical (manufactured by Wako Pure Chemical Industries, Ltd.)
Sodium hydroxide (NaOH): Special grade chemical (manufactured by Wako Pure Chemical Industries, Ltd.)

2. Analysis Method

[Acid Number]

An acid number of GBL was measured by the following method.

In a 100-mL beaker, 60 mL of distilled water was charged, a nitrogen pipe was inserted into the liquid, and nitrogen was blown thereinto while stirring with a stirrer, thereby achieving deaeration. Subsequently, a 0.001 mol/L ammonia aqueous solution was added dropwise while measuring a pH with a pH meter (F-74BW, manufactured by Horiba, Ltd.), thereby adjusting the pH to 6.8 to 7.0.

When the pH became stable, the nitrogen pipe was taken out, 10 mL of a GBL sample that is subjective to the measurement was added, and the resultant was titrated with a 0.02 mol/L potassium hydroxide standard liquid while stirring with a stirrer, until the pH reached 7.0. The acid number was calculated according to the following equation. f=1.026 was used.

$$\text{Acid number (mg-KOH/g)}=(V \times f \times 1.122)/(10 \times 1.130)$$

V: Titer (mL) of 0.02 mol/L potassium hydroxide standard liquid
f: Factor of 0.02 mol/L potassium hydroxide standard liquid
10: Sample collection amount (mL)
1.130: Specific gravity of GBL (20/4° C.)
1.122: Acid number corresponding amount (g) of 1 mL of 0.02 mol/L potassium hydroxide standard liquid

[Absorbance Analysis]

A sample was put into a 10-mm quart cell, and its absorbance at a wavelength of 450 nm was measured with a spectrophotometer (UV-2000 Model, manufactured by Hitachi, Ltd.).

[Gas Chromatography Analysis]

GBL was analyzed with a gas chromatography analysis apparatus (GC-17A Model, manufactured by Shimadzu Corporation) by using a DB-1 column (non-polar), manufactured by Agilent.

3. EXAMPLES 3-1. Effect by Containing of Nitrogen-Containing Compound

Example 1

1 ppm of NMP was added to GBL (purity: 99.95% or more). As a result of measurement of an acid number of this GBL composition, the acid number was found to be 0.16 mg-KOH/g. In addition, as a result of measurement of an electrical conductance, the electrical conductance was found to be 0.36 μS/cm. The analysis results are shown in Table 3.

Examples 2 to 4

The acid number and the electrical conductance were measured in the same manners as in Example 1, except that the addition amount of NMP was changed to 10 ppm, 100 ppm, and 1,000 ppm, respectively. The analysis results are shown in Table 3.

Examples 5 to 12

The same procedures as in Example 1 were followed, except that 2-pyrrolidone (2P) or succinic acid diamide was added in a varied concentration in place of NMP. The analysis results are collectively shown in Table 3.

Comparative Example 1

The acid number and the electrical conductance were measured without adding any material to GBL (purity: 99.95% or more, nitrogen-containing compound: less than 0.1 ppm-N). The analysis results are shown in Table 3.

TABLE 3

| | Main component | Nitrogen-containing compound | Concentration ppm | Nitrogen atom concentration ppm-N | Acid number mg-KOH/g | Electrical conductance μS/cm |
|---|---|---|---|---|---|---|
| Example 1 | GBL | NMP | 1 | 0.1 | 0.16 | 0.36 |
| Example 2 | GBL | NMP | 10 | 1.4 | 0.15 | 0.43 |
| Example 3 | GBL | NMP | 100 | 14 | 0.14 | 0.44 |
| Example 4 | GBL | NMP | 1000 | 141 | 0.10 | 0.44 |

TABLE 3-continued

| | Main component | Nitrogen-containing compound | Concentration ppm | Nitrogen atom concentration ppm-N | Acid number mg-KOH/g | Electrical conductance µS/cm |
|---|---|---|---|---|---|---|
| Example 5 | GBL | 2-Pyrrolidone | 1 | 0.2 | 0.16 | 0.39 |
| Example 6 | GBL | 2-Pyrrolidone | 10 | 1.6 | 0.14 | 0.40 |
| Example 7 | GBL | 2-Pyrrolidone | 100 | 16 | 0.13 | 0.43 |
| Example 8 | GBL | 2-Pyrrolidone | 1000 | 165 | 0.10 | 0.44 |
| Example 9 | GBL | Succinic acid diamide | 1 | 0.2 | 0.16 | 0.36 |
| Example 10 | GBL | Succinic acid diamide | 10 | 2.4 | 0.14 | 0.42 |
| Example 11 | GBL | Succinic acid diamide | 100 | 24 | 0.13 | 0.55 |
| Example 12 | GBL | Succinic acid diamide | 1000 | 241 | 0.13 | 0.55 |
| Comparative Example 1 | GBL | — | <0.1 | <0.1 | 0.17 | 0.20 |

From comparison of Examples 1 to 12 with Comparative Example 1, it is noted that in the GBL composition of the present invention, by containing a specified amount of the nitrogen-containing compound, the acid number is lead low, and the adverse influence by the acid component in the case of being used as an electrolytic solution or the like can be expected to be inhibited. In addition, the GBL composition of the present invention has a high electrical conductance, so that it is noted that the GBL composition of the present invention is high in industrial use value for an electrolytic solution for capacitors and the like.

Examples 13 and 14

A solution obtained by stirring a solution of GBL (purity: 99.95% or more) having 100 ppm or 1,000 ppm of NMP added thereto at 150° C. for 2 hours was slightly colored yellow. An absorbance at 260 nm of each of the resulting solutions was measured. The analysis results are shown in Table 4.

Comparative Example 2

An absorbance was measured in the same manner as in Example 13, except that the addition amount of NMP was changed to 8,000 ppm. The analysis results are shown in Table 4.

Examples 15 and 16

A solution obtained by stirring a solution of GBL (purity: 99.95% or more) having 1,000 ppm of FMS and 1 ppm or 1,000 ppm of NMP added thereto at 150° C. for 2 hours was slightly colored yellow. An absorbance at 260 nm of each of the resulting solutions was measured. The analysis results are shown in Table 4.

Comparative Example 3

An absorbance was measured in the same manner as in Example 15, except that the addition amount of NMP was changed to 8,000 ppm. The analysis results are shown in Table 4.

Examples 17 and 18

An absorbance was measured in the same manner as in Examples 15 and 16, except that 100 ppm of NaOH was added in place of FMS. The analysis results are shown in Table 4.

Comparative Example 4

An absorbance was measured in the same manner as in Example 17, except that the addition amount of NMP was changed to 8,000 ppm. The analysis results are shown in Table 4.

Examples 19 and 20

A solution obtained by stirring a solution of GBL (purity: 99.95% or more) having 400 ppm or 2,000 ppm of succinic acid diamide added thereto at 150° C. for 2 hours was slightly colored yellow. An absorbance at 260 nm of each of the resulting solutions was measured. The analysis results are shown in Table 4.

Comparative Example 5

An absorbance was measured in the same manner as in Example 19, except that the addition amount of succinic acid diamide was changed to 5,000 ppm. The analysis results are shown in Table 4.

TABLE 4

| | Main component | Nitrogen-containing compound | Concentration ppm | Nitrogen atom concentration ppm-N | FMS concentration ppm | NaOH concentration ppm | Absorbance at 260 nm |
|---|---|---|---|---|---|---|---|
| Example 13 | GBL | NMP | 100 | 14 | — | — | 1.1 |
| Example 14 | GBL | NMP | 1000 | 141 | — | — | 1.9 |
| Comparative Example 2 | GBL | NMP | 8000 | 1131 | — | — | 2.6 |
| Example 15 | GBL | NMP | 1 | 0.14 | 1000 | — | 5.0 |
| Example 16 | GBL | NMP | 1000 | 141 | 1000 | — | 4.4 |
| Comparative Example 3 | GBL | NMP | 8000 | 1131 | 1000 | — | 13.4 |
| Example 17 | GBL | NMP | 1 | 0.14 | — | 100 | 0.1 |
| Example 18 | GBL | NMP | 1000 | 141 | — | 100 | 0.7 |

TABLE 4-continued

| | Main component | Nitrogen-containing compound | Concentration ppm | Nitrogen atom concentration ppm-N | FMS concentration ppm | NaOH concentration ppm | Absorbance at 260 nm |
|---|---|---|---|---|---|---|---|
| Comparative Example 4 | GBL | NMP | 8000 | 1131 | — | 100 | 5.8 |
| Example 19 | GBL | Succinic acid diamide | 400 | 97 | — | — | 3.8 |
| Example 20 | GBL | Succinic acid diamide | 2000 | 483 | — | — | 4.1 |
| Comparative Example 5 | GBL | Succinic acid diamide | 5000 | 1207 | — | — | 4.2 |

From comparison of Examples 13 to 20 with Comparative Examples 2 to 5, it is noted that in the GBL compositions where the nitrogen-containing compound is contained in an excessive amount as compared with the amount prescribed in the present invention, the hue is remarkably deteriorated by heating. The remarkable deterioration of the hue is caused by polymerization due to the nitrogen-containing compound.

3-2. Effect of Acid Number

Examples 21 to 24

A solution in which 1 ppm of NMP was added to GBL (purity: 99.95% or more), and 100 ppm or 1,000 ppm of NaOH, or 1,000 ppm or 8,000 ppm of FMS was further added was stirred at 150° C. for 2 hours. The resulting solution was subjected to gas chromatography analysis, and a reduction amount of GBL after heating was calculated. The analysis results are shown in Table 5.

Examples 25 to 30

A solution in which 50 ppm of NMP was added to GBL (purity: 99.95% or more), and 10 ppm, 100 ppm, or 1,000 ppm of NaOH, or 100 ppm, 1,000 ppm, or 8,000 ppm of FMS was further added was stirred at 150° C. for 2 hours. The resulting solution was subjected to gas chromatography analysis, and a reduction amount of GBL after heating was calculated. The analysis results are shown in Table 5.

Examples 31 to 34

A solution in which 1,000 ppm of NMP was added to GBL (purity: 99.95% or more), and 100 ppm or 1,000 ppm of NaOH, or 1,000 ppm or 8,000 ppm of FMS was further added was stirred at 150° C. for 2 hours. The resulting solution was subjected to gas chromatography analysis, and a reduction amount of GBL after heating was calculated. The analysis results are shown in Table 5.

TABLE 5

| | Main component | NMP concentration ppm-N | Nitrogen atom concentration ppm-N | FMS concentration ppm | NaOH concentration ppm | Acid number mg-KOH/g | Reduction amount of GBL after heating % by mass |
|---|---|---|---|---|---|---|---|
| Example 21 | GBL | 1 | 0.14 | — | 100 | 0.11 | 0.9 |
| Example 22 | GBL | 1 | 0.14 | — | 1000 | 0.04 | 3.4 |
| Example 23 | GBL | 1 | 0.14 | 1000 | — | 0.46 | −0.2 |
| Example 24 | GBL | 1 | 0.14 | 8000 | — | 1.63 | 5.8 |
| Example 25 | GBL | 50 | 7 | — | 10 | 0.14 | 0.9 |
| Example 26 | GBL | 50 | 7 | — | 100 | 0.10 | 0.8 |
| Example 27 | GBL | 50 | 7 | — | 1000 | 0.03 | 2.7 |
| Example 28 | GBL | 50 | 7 | 100 | — | 0.33 | −0.1 |
| Example 29 | GBL | 50 | 7 | 1000 | — | 0.48 | 0.8 |
| Example 30 | GBL | 50 | 7 | 8000 | — | 1.22 | 7.6 |
| Example 31 | GBL | 1000 | 141 | — | 100 | 0.10 | −0.9 |
| Example 32 | GBL | 1000 | 141 | — | 1000 | 0.01 | 3.9 |
| Example 33 | GBL | 1000 | 141 | 1000 | — | 0.45 | 0.5 |
| Example 34 | GBL | 1000 | 141 | 8000 | — | 1.63 | 6.5 |

In the present invention, it is noted that by further allowing the acid number to fall within a specified range, the thermal stability of the GBL composition can be more improved.

While the invention has been described in detail and with reference to specific embodiments thereof, it will be apparent to one skilled in the art that various changes and modifications can be made therein without departing from the spirit and scope thereof. It is to be noted that the present application is based on a Japanese patent application filed on Feb. 17, 2014 (Japanese Patent Application No. 2014-027766), and the contents are incorporated herein by reference.

The invention claimed is:

1. A gamma-butyrolactone composition, comprising:
   gamma-butyrolactone; and
   a nitrogen-containing compound,
   wherein a content of the gamma-butyrolactone is 99.0% by mass or more, and a total content of the nitrogen-containing compound is 0.1 ppm by mass to 1,000 ppm by mass as converted to a nitrogen atom.
2. The gamma-butyrolactone composition according to claim 1,
   wherein an acid number is 10 mg-KOH/g or less.
3. The gamma-butyrolactone composition according to claim 1,
   wherein an acid number is 0.05 to 0.9 mg-KOH/g.

4. The gamma-butyrolactone composition according to claim 1,
wherein an acid number is 0.05 to 0.5 mg-KOH/g.

5. The gamma-butyrolactone composition according to claim 1,
wherein a difference between a boiling point at atmospheric pressure of the nitrogen-containing compound and a boiling point at atmospheric pressure of the gamma-butyrolactone is within 50° C.

6. The gamma-butyrolactone composition according to claim 1,
wherein a molecular weight of the nitrogen-containing compound is 1,000 or less.

7. The gamma-butyrolactone composition according to claim 1,
wherein the nitrogen-containing compound is a compound represented by formula (1):

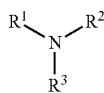
(1)

wherein $R^1$ to $R^3$ each independently represent a hydrogen atom, an alkyl group, an alkenyl group, an aryl group, an alkoxy group, a hydroxyl group, an amino group, an amide group, an alkylthio group, an arylthio group, an alkylcarbonyl group or an arylcarbonyl group; each of $R^1$ to $R^3$ may further have a substituent; a hetero atom may be contained in the substituent; and two groups selected from $R^1$ to $R^3$ may be bonded to each other to form a ring, provided that a sum total of the carbon atom number of $R^1$ to $R^3$ is 1 or more and 50 or less.

8. The gamma-butyrolactone composition according to claim 1,
wherein the nitrogen-containing compound is at least one of 2-pyrrolidone and N-methylpyrrolidone.

9. A method for producing a gamma-butyrolactone composition containing gamma-butyrolactone and a nitrogen-containing compound, in which a content of the gamma-butyrolactone is 99.0% by mass or more, and a total content of the nitrogen-containing compound is 0.1 ppm by mass to 1,000 ppm by mass as converted to a nitrogen atom,
wherein the nitrogen-containing compound is a compound derived from succinic acid or a succinic acid derivative, and
the method comprises the following steps (1) to (3):
Step (1): a step of subjecting succinic acid or a succinic acid derivative to hydrogenation reaction to obtain crude gamma-butyrolactone;
Step (2): a step of distilling the gamma-butyrolactone to distill off a low boiling compound and a high boiling compound; and
Step (3): a step of flowing the gamma-butyrolactone obtained in the step (2) through a cation exchange resin to achieve purification.

* * * * *